(12) United States Patent
Mautone

(10) Patent No.: US 6,676,930 B2
(45) Date of Patent: *Jan. 13, 2004

(54) COMPOSITION AND METHOD FOR TREATMENT OF OTITIS MEDIA

(75) Inventor: Alan J. Mautone, Morristown, NJ (US)

(73) Assignee: Scientific Development and Research, Inc., Belleville, NJ (US)

( * ) Notice: Subject to any disclaimer, the term of this patent is extended or adjusted under 35 U.S.C. 154(b) by 23 days.

This patent is subject to a terminal disclaimer.

(21) Appl. No.: 10/011,344

(22) Filed: Dec. 4, 2001

(65) Prior Publication Data

US 2002/0064503 A1 May 30, 2002

Related U.S. Application Data

(63) Continuation-in-part of application No. 09/639,682, filed on Aug. 16, 2000, which is a continuation of application No. 09/450,884, filed on Nov. 28, 1999, now Pat. No. 6,156,294.

(51) Int. Cl.[7] .................. A61M 11/04; A61M 15/02; A61K 9/12; A61K 9/72
(52) U.S. Cl. .................. 424/45; 128/200.23
(58) Field of Search .................. 424/45; 128/200.23

(56) References Cited

U.S. PATENT DOCUMENTS

| | | |
|---|---|---|
| 4,814,161 A | 3/1989 | Ajinks et al. |
| 4,826,821 A | 5/1989 | Clements |
| 4,895,719 A | 1/1990 | Radhekrishnan |
| 4,931,284 A | 6/1990 | Ekman et al. |
| 4,973,465 A | 11/1990 | Baurain et al. |
| 5,004,611 A | 4/1991 | Leigh |
| 5,013,720 A | 5/1991 | Whitsett |
| 5,024,995 A | 6/1991 | Robertson et al. |
| 5,049,389 A | 9/1991 | Radhakrishnan |
| 5,053,217 A | 10/1991 | Lehigh |
| 5,134,129 A | 7/1992 | Lichtenberger |
| 5,141,674 A | 8/1992 | Leigh |
| 5,174,988 A | 12/1992 | Mautone et al. |
| 5,299,566 A | 4/1994 | Davis et al. |
| 5,302,581 A | 4/1994 | Sarin et al. |
| 5,306,483 A | 4/1994 | Mautone |
| 5,387,746 A | 2/1995 | Whitsett |
| 5,401,741 A | 3/1995 | Sato et al. |
| 5,407,914 A | 4/1995 | Cochrane et al. |
| 5,415,867 A | 5/1995 | Minchey et al. |
| 5,470,587 A | 11/1995 | Bartolmeo |
| 5,618,786 A | 4/1997 | Roosdorp et al. |
| 5,663,198 A | 9/1997 | Reul et al. |
| 5,789,381 A | 8/1998 | Cochrane et al. |
| 5,855,913 A | 1/1999 | Hanes et al. |
| 5,925,334 A | 7/1999 | Rubin et al. |
| 5,952,008 A | 9/1999 | Backstrom et al. |
| 5,952,303 A | 9/1999 | Bornstein et al. |
| 6,001,870 A | 12/1999 | Henkyl |
| 6,093,417 A | 7/2000 | Petrus |
| 6,129,934 A | 10/2000 | Egan et al. |
| 6,136,295 A | 10/2000 | Edwards et al. |
| 6,143,276 A | 11/2000 | Unger |
| 6,156,294 A * | 12/2000 | Mautone .................. 424/45 |
| RE37,053 E | 2/2001 | Hanes et al. |
| 6,200,598 B1 | 3/2001 | Needham |
| 6,264,922 B1 | 7/2001 | Wood |
| 6,297,227 B1 | 10/2001 | Johnson |
| 6,309,623 B1 | 10/2001 | Weers et al. |

FOREIGN PATENT DOCUMENTS

| | | |
|---|---|---|
| WO | WO 88/01862 | 3/1988 |
| WO | WO 96/27393 | 9/1996 |
| WO | WO97/29738 | 8/1997 |
| WO | WO 99/33472 * | 7/1999 |

* cited by examiner

Primary Examiner—Frederick Krass
Assistant Examiner—Donna Jagoe
(74) Attorney, Agent, or Firm—Richard L. Strauss, Esq.

(57) ABSTRACT

A process, composition and method for increasing and enhancing mammalian eustachian tube lumen patency and pressure equalization performance is disclosed wherein an aerosolized mixture of lipid crystals comprised of a mixture of one or more lipids surfactants and one or more spreading agents selected from the group consisting of sterols, lipids, fatty acids, cholesteryl esters, phospholipids, carbohydrates, and proteins, in powder form, and one or more propellants, in which the lipid surfactants and spreading agents are not soluble, are administered through a mammalian airway orifice. Upon administration, the propellant(s) are evaporated from the mixture and the lipid crystals are deposited within a subject mammalian eustachian tube whereupon said lipid crystals come into contact with lumen surfaces of the tube forming an amorphous spread film thereupon substantially decreasing the opening pressure of the lumen. In a second preferred embodiment, a therapeutically active agent effective in the treatment of otitis media is added to the mixture of lipid crystals and upon administration of said aerosol mixture, the amorphous spread film formed thereby carries said therapeutically active agent through the eustachian tube to the tissues of the middle ear. In an alternate preferred embodiment, the afore-mentioned reduction of surface tension and delivery of therapeutically active agents is provided by a mixture of lipid crystals comprised of surfactant(s), therapeutically active agents and a propellant in which such other components are not soluble.

68 Claims, No Drawings

COMPOSITION AND METHOD FOR TREATMENT OF OTITIS MEDIA

RELATED APPLICATIONS

This application is a continuation-in-part of U.S. patent application Ser. No. 09/639,682 filed on Aug. 16, 2000, which said application is a continuation of U.S. patent application Ser. No. 09/450,884 filed Nov. 28, 1999 and issued as U.S. Pat. No. 6,156,294 on Dec. 5, 2001.

FIELD OF INVENTION

The present invention relates to the field of pharmacological compositions and methods of utilizing such compositions in order to improve the flow of both naturally occurring fluids and pharmacologic agents through the mammalian eustachian tube.

BACKGROUND OF THE INVENTION

Otitis media is a pathological condition common to mammalian species and most common to children. During episodes of otitis media, fluid accumulates in the middle ear or, as it is also known, the tympanic cavity.

Acute otitis media is a condition in which fluid accumulation in the middle ear is accompanied by signs or symptoms of ear infection (including both viral and bacterial etiologies). Such pathology may exhibit a bulging eardrum accompanied by pain or, in some instances, perforation of the tympanic membrane. Such perforations may also be accompanied by drainage of purulent material. In contrast, otitis media with effusion is typified by fluid accumulation within the tympanic cavity without signs of infection.

Both acute otitis media and otitis media with effusion may cause substantial pain as pressure increases, positively or negatively, within the confines of the tympanic chamber. Antibiotics, steroids, and antibiotics in combination with steroids have been utilized to treat otitis media. Antihistamine/decongestants have also been utilized in the treatment of otitis media with effusion.

The anatomical features of the middle ear define what can be described as a sealed chamber. On its lateral border, the middle ear is effectively isolated from the external auditory meatus (in the absence of a punctured ear drum), by the tympanic membrane. Medially, the middle ear is effectively sealed from the inner ear by a bony wall. The posterior wall of the tympanic cavity communicates with a large, but effectively sealed mastoid antrum. Only the anterior wall of the middle ear contains a passageway for effective communication outside of the tympanic cavity. There, a natural pathway provided by the auditory or, as it is also known, the eustachian tube, provides communication with the nasopharynx.

As stated above, during episodes of acute otitis media, the painful increased middle ear pressure may naturally resolve through a resultant perforation of, and drainage through, the tympanic membrane. However, the increased fluid pressure associated with otitis media with effusion does not resolve via this mechanism. In fact, for those patients suffering otitis media for prolonged periods of time, and especially for those evidencing significant associated hearing loss, myringotomy with the placement of a tympanostomy tube may be indicated as a means of equalizing middle ear pressure and in order to restore normal hearing. Recently, laser surgery has also been utilized to provide an aperture through the tympanic membrane through which the fluid trapped within the middle ear may drain. Besides the perforations of the eardrum provided by infection (acute otitis media), myringotomy and laser surgery, the eustachian tube, a natural middle ear drainage path described above, is provided by mammalian anatomy. Unfortunately, during episodes of otitis media with effusion (OME), a time when the natural pathway and pressure relief functions of the eustachian tube would be most useful, the increase pressure required to open the lumen (as described in more detail above and below), effectively eliminates this means of relieving middle ear pressurization. Reduced patency of the eustachian tube is believed to be one of the primary causes of OME in pediatric patients. In fact, it is known that OME elevates eustachian tube opening pressure independent of other pathological conditions effecting this conduit. The term "opening pressure" as it is utilized throughout this disclosure and within the claims, refers to the pressure, typically measured in millimeters of mercury, necessary to cause the lumen of the auditory tube to open and provide a patent pathway between the nasopharynx and tympanic cavity.

Treatment of otitis media by means of administration of anti-inflammatory agents, antibiotics, decongestants and/or anti-histamines, or combinations thereof, is limited in effectiveness as, in the absence of perforation, there is presently no method for direct application of such drugs directly to target tissues of the eustachian tube and/or middle ear. Systemic applications of drugs via parenteral or oral routes, while eventually reaching the eustachian tube and middle ear, may have adverse systemic effects and, more importantly, are not especially effective at delivering a concentrated dose of the applicable drugs where they are truly needed, directly to the target tissues. Simply put, the sealed chamber anatomy of the middle ear has, up until the present time, constituted a barrier to direct drug application.

Although the central lumen of the eustachian tube does provide a pathway to the tympanic cavity, it is, as described below, ordinarily closed and resistant to fluid passage due to its inherent anatomical configuration. During episodes of otitis media, the relatively high surface tensions present at the air/liquid interface located upon the epithelial lining of the tube lumen further increase the opening pressure required to open this channel. Although direct application of therapeutically active agents, effective in the treatment of otitis media, to the lumen of the eustachian tube, and via the lumen to the middle ear, would be highly advantageous in treating otitis media, no method or composition has yet been disclosed capable of overcoming the surface tension within the tube lumen so as to facilitate opening of the tube and transport of such drugs throughout the lumen and on to the tissues of the middle ear. What is needed is a composition and method of applying same, especially formulated and adapted to decrease the surface tension of the auditory tube so as to decrease the opening pressure thereof, thereby providing a patent conduit for therapeutic agents, effective in the treatment of otitis media, to travel through said tube to effectively treat said condition.

Pathological conditions can arise from, and can cause changes in surface tension values of air/liquid interfaces in other organs of mammalian anatomy. The naturally occurring "surfactant system" secreted upon the epithelial lining of the lung which is deficient in cases of R.D.S. is known to be comprised of a complex mixture of lipids, proteins and carbohydrates (as described in a recent review: Surfactants and the Lining of the Lung, The John Hopkinds University Press, Baltimore, 1988). The prime function of the surfactant system is to stabilize the alveoli and associated small airways against collapse by decreasing the surface tension at the air/liquid interface. It is now believed that the action of the phospholipid component of the surfactant system is the principal source of the powerful surface tension reduction effect of the naturally occurring surfactant system of the lung. More specifically, it is known that the fully saturated diacylphospholipids, principally, dipalmitoyl phosphatidylcholine (DPPC) provide liquid balance and anti-collapse properties to the lung's epithelial lining. In addition to DPPC, spreading agents, also found within the naturally occurring surfactant system, assist DPPC in rapidly forming a uniform spread film on the air/liquid surfaces of the lung. Such spreading agents include cholesteryl esters such as, for example, cholesteryl palmitate (CP); phospholipids such as, for example, diacylophosphatidylglycerols (PG), diacylphosphatidylethanolamines (PE), diacylphosphatidylserines (PS), diacylphosphatidylinositols (PI), sphingomelin (Sph) and Cardiolipin (Card); and virtually and other phospholipid, and of the lysophospholipids; or any of the plasmalogens, dialklylphospholipids, phosphonolipids, carbohydrates and proteins, such as, for example, albumin, pulmonary surfactant proteins A, B, C and D. The naturally occurring surfactant system is further described in U.S. Pat. No. 5,306,483.

DPPC has been administered to infants with respiratory distress syndrome as a therapeutic measure. For this purpose, DPPC has been administered by means of an aqueous aerosol generator (utilized with an incubator in which the infant resided during treatment). Endotracheal administration has also been utilized. DPPC therapy has been typified as utilizing natural surfactants (harvested from porcine or bovine lungs), or artificial, commercially synthesized compounds.

It has also heretofore been disclosed to utilize therapeutic agents, in combination with surfactant/spreading agents to effectively administer drug therapy uniformly throughout the epithelial lining of the lung. U.S. Pat. No. 5,306,483 (the "'483 patent") discloses a process to prepare lipid crystalline figures in fluorocarbon propellants for the delivery of therapeutically active substances which form amorphous fluids on delivery at the air/liquid interface of the lung and which can be utilized as an effective drug delivery system. More specifically, said patent discloses a process comprising (a) preparing a mixture of one or more lipids of the group of phospholipids known as phosphatidylcholines and one or more spreading agents, in powder form and a therapeutically active substance and one or more fluorocarbon propellants, said lipids, spreading agents and therapeutically active substances being insoluble in the propellants; and (b) evaporating the propellants from the mixture. The '483 patent teaches the combination of dipalmitoyl phosphatidylcholine (DPPC) or any of the other fully saturated Acyl chain phospholipids, 80.0 to 99.5% by weight, and other spreading agents, for example, phospholipids such as, but not limited to PG, PE, PS, PI, lysophospholipids, plasmalogens, dialkylphospholipids, diether phosphonolipids, Cardiolipin, sphingomyelin, 0.5 to 20.0% weight, neutral lipids like cholesteryl esters such as, but no limited to, cholesteryl palmitate, cholesteryl oleate, cholesteryl stearate or mixtures thereof, 0.5 to 10% by weight, carbohydrates, such as, but not limited to, glucose, fructose, galactose, pneumogalactan, dextrose (or mixtures thereof), 0.5 to 10% by weight, and proteins such as, but not limited to albumin, pulmonary surfactant specific proteins A, B, C, and D 0.5 to 10% by weight, compounds in lipid-crystalline structures in fluorocarbon (both chloro- and hydrofluorocarbon) propellants in which therapeutically active agents, drugs and other materials can be carried into the lungs after release from and through metered dose nebulizer. The spreading agents referred to in the '483 patent are compounds such as the above-described phospholipids, lysophospholipids, plasmalogens, dialklyphospholipids, phosphonolipids, carbohydrates and proteins. The function of the spreading agent is to assist DPPC, or other phospholipids such as, for example, DPPG, in rapidly adsorbing and forming a spread film upon the air/liquid surfaces of the lungs. In addition, the '483 patent also discloses a process for preparing such lipid crystalline figures in fluorocarbon propellants without a therapeutically active substance for use as a tear (as for the eye).

Although the '483 patent does disclose a process for preparing a drug delivery system especially adapted for uniformly applying a therapeutic agent to the epithelial lining of the lung, heretofore, no method or composition has been disclosed in the past that is particularly adapted, configured and formulated for the delivery of therapeutic agents to target tissues of the eustachian tube, or, via the eustachian tube, the middle ear.

Otitis media can, due to fluid accumulation, cause significant pressure, both positive and negative, in the aforementioned confines of the middle ear. Pressure differentials between the middle ear and the surrounding atmosphere, whether due to the addition of such fluids, or due to the relative decrease or increases of ambient atmospheric pressure, can cause great pain and discomfort. Such pressure conditions subject the tympanic membrane, and the associated pain receptors, to bulging and stretching. In addition, the accumulation of fluids, and the resulting static tension applied to the tympanic membrane, can greatly reduce hearing.

As mentioned above, the eustachian tube is specifically adapted to provide communication between the middle ear (a sealed chamber), and ambient atmospheric pressure, by providing a pathway between the tympanic cavity and the nasopharynx. Thus the auditory tube serves as a pressure equalization means for the middle ear. However, in order to provide this equalization function, and, at the same time, allow proper middle ear sound conduction, the eustachian tube, and the pathway it provides between the middle ear and the nasopharynx, are ordinarily closed. The lumen of the tube, as discussed below, is ordinarily open only during the act of swallowing and other movements that cause contraction of the attached musculature.

In humans, the eustachian tube is, on the average, 3.5 cm in length. The posterior one third of the tube is comprised of a bony wall with the anterior two thirds of the tubular structure being cartilaginous in composition. The auditory tube provides, by means of a central lumen, a fluid passage way between the nasopharynx and middle ear. However, the somewhat flattened medial and lateral walls of the tube are ordinarily in direct contact occluding and effectively limiting passage of liquids and gasses therethrough and allowing optimal sound conduction function of the middle ear which requires a sealed chamber. During swallowing, the tensor veli palatini muscle, which inserts into the lateral surface of the cartilaginous portion of the tube, contracts and pulls the wall of the tube laterally opening the central lumen thereby providing the communicating pathway needed for fluid flow between the middle ear and the nasopharynx. The action of the muscle upon the tube is needed to overcome the surface tension attracting the flattened medial and lateral walls of the central lumen together as well as the elastic recoil of the tube cartilage which also tends to close the lumen. The surface tension is due to the sero-mucous secretions found on the epithelial lining of the lumen.

In normal physiologic function, the sero-mucous secretions of the auditory tube, and the relatively low surface tensions they produce at the lateral and medial walls of the lumen, do not interfere with the normal opening and related pressure equalization functions of the auditory tube. However, middle ear, tube and upper respiratory infections and/or inflammatory conditions, such as allergies, can greatly effect the nature and increase the amount of the secretions found upon the lumen surface. Generally, such pathologic conditions greatly increase the surface tension of the lumen walls by increasing the relative amount of mucoid secretions, effectively interfering with, or completely preventing the opening of the tube. In addition, the tissues of the eustachian tube may become inflamed and engorged with fluids and cause further increases in opening pressures.

The above-described alterations in the nature and amount of secretions as well as inflammation of tube tissues are common during episodes of otitis media. Therefore, at a time when eustachian tube drainage of the middle ear would be highly desirable, this normally effective physiologic means of eliminating painful pressure often associated with such pathology is either hindered or completely eliminated. The common cold, flu, hay fever and other allergies can also result in eustachian tube failure for the same reason. However, inflammatory changes in tube tissues and lumen secretions are not the exclusive cause of such auditory tube failures.

Rapid changes in ambient pressure may also inhibit or completely prevent normal equalization functions of the auditory tube. If ambient pressure changes too quickly, the pressure gradient between the atmosphere and tympanic cavity may be too great to allow lumen opening. For example, the pressure within the tympanic cavity of a diver who, for example, ascends from a relatively deep dive without effectively and continuously equilibrating his or her middle ear through action of the eustachian tube (by swallowing, wiggling the jaw or utilizing other means to contract the attached musculature) can experience terrific pain know as a "squeeze" which may be very difficult to overcome. Such situations are more likely in such instances when, for example, a diver engages in such activity, wisely or unwisely, while he is or she is suffering from an allergy or cold (for the above-described reasons). By rising in depth without frequent and effective eustachian tube function, the relatively low ambient pressure surrounding the diver effectively seals off the eustachian tubes communication with the relatively highly pressurized middle ear. A diver, under such circumstances, may simply descend back a few feet to a depth where the pressure gradient is non-existent or minimal, and thereby lower the opening pressure of the auditory tube allowing it to open and equalize the tympanic cavity. However, a passenger on a plane is in no position to change altitudes to obtain a "second chance" to equilibrate. If such a passenger is unable to frequently and effectively equilibrate the middle ear during altitude changes due to, for example, increased secretions within the tube resulting from a cold, he or she is forced to bear significant pain.

Although, as described below, surfactant compositions, both natural and artificial, have been heretofore known, formulated and utilized to decrease surface tension within the lung, no such compositions, processes or methods for administering said compositions, have been heretofore suggested, taught or disclosed in regards to decreasing the surface tension within the lumen of the eustachian tube. Likewise, no method has heretofore been known which provides an effective decrease in opening resistance of the eustachian tube while simultaneously providing the delivery of therapeutically active agents, effective in the treatment of otitis media directly to the epithelial lining of the eustachian tube and middle ear.

SUMMARY OF THE INVENTION

Now, in accordance with the present invention, a method of increasing and enhancing mammalian eustachian tube lumen patency and pressure equalization performance is disclosed.

In a first preferred embodiment of the present invention, a mixture of one or more lipids and one or more spreading agents selected from the group consisting of sterols, lipids, fatty acids, cholesteryl esters, phospholipids, carbohydrates, and proteins, all in powder form, and one or more propellants is prepared. The propellant is selected to be one in which the one or more lipids and one or more spreading agents are not soluble so as to enable, in part, the formation of the below-described lipid crystals. Propellants such as, for example, fluorocarbon propellants may be advantageously selected. The lipids and the spreading agents are likewise advantageously selected to be insoluble in the propellants.

The lipid surfactants utilized in practicing the method of the present invention are selected to be present in an amount sufficient to effectively reduce the surface tension of the liquid/air interface of the epithelial surface to which they are applied, while the spreading agents are present in an amount sufficient to effectively distribute the lipids upon said surface. The term, "effectively reduce surface tension" as utilized throughout this application and in the claims, refers to that weight percentage range of lipid which, when present in said mixture of lipid crystals, provides a clinically significant decrease in eustachian tube opening pressure so as to allow increased pressure equalization function. The term, "effectively distribute the lipids upon said surface" refers to that weight percentage range of spreading agent that is required in order to provide adequate spreading and distribution of the lipids so as to form an amorphous spread film upon the epithelial lined surfaces of the lumen so that the lipid surfactant effects sufficient lumenal surface area enabling the afore-mentioned reduction in opening pressure.

It has been found that the above-described clinically significant decrease in eustachian tube opening pressure and effective distribution of lipids can be effected by a mixture comprised of from about 99.99 to about 30 weight percent lipid surfactant and from about 70 to about 0.01 spreading agent. Increased effectiveness is provided by a preferred mixture comprised of from about 99.99 to about 50 weight percent lipid surfactant and from about 50 to about 0.01 weight percent spreading agent, both based on total weight of the mixture. However, it is still further preferred that the lipid surfactants utilized in practicing the method of the present invention are present in an amount of about 80 to 99.5 percent by weight and the spreading agents are present in an amount of about 0.5 to about 20 percent by weight, both based upon the total weight of the mixture. Combination of the one or more lipids, one or more spreading agents and one or more propellants results in the formation of lipid crystals described in more detail, below. A metered dose of the mixture of lipid crystals is then administered, via inhalation through an external airway, into a mammal upon which the present method is practiced. It is preferred that the mixture be administered via a nasal orifice. However, it is also contemplated that the mixture of lipid crystals may also be administered via oral inhalation.

Upon administration, the propellant(s) are evaporated from the mixture and the lipid crystals are deposited at a nasopharyngeal, or as it may also be described, an anterior terminus, of a subject mammalian eustachian tube whereupon said lipid crystals come into contact with lumen surfaces of the tube. Upon contact with the air/liquid interfaces of the eustachian tube lumen, the mixture of lipid crystals forms an amorphous spread film upon said air/liquid interface effectively decreasing the opening pressure thereof.

The lipid crystals deposited upon the lumen surfaces and air/liquid interface thereupon is comprised of one or more lipids which are advantageously selected to demonstrate powerful surfactant activity. In addition, the spreading agent combined therewith provides substantially complete distribution of the surfactant over and upon the air/liquid interface resident upon the epithelial lining thereby resulting in a substantial decrease in lumen opening pressure. In turn, the decrease in lumen opening pressure results in greater patency of the eustachian tube and provides a resultant increase in fluid conduction/equalizing function of this anatomical structure.

In a second preferred embodiment of the present invention, a method of administering therapeutically active agents, effective in the treatment of otitis media, directly to mammalian eustachian tube and middle ear target tissues as well as a process for preparing a medicament for providing such treatment is disclosed. In the second embodiment of the present invention, a mixture of one or more lipids, one or more spreading agents, one or more therapeutically active agent(s), effective in the treatment of otitis media, and one or more propellants is prepared. The one or more lipids and spreading agents are advantageously selected from the group consisting of lipids, fatty acids, cholesteryl esters, phospholipids, carbohydrates, and proteins, all being in powder form. The one or more lipid surfactant, spreading agents and therapeutically active agent(s), effective in the treatment of otitis media, and the propellants are selected so that the lipid surfactants and spreading agents are insoluble in the propellants. The lipids utilized in practicing the method of the second preferred embodiment of the present invention are selected to be present in an amount sufficient to effectively reduce the surface tension of the liquid/air interface of the epithelial lining to which they are applied, while the spreading agents are present in an amount sufficient to effectively distribute the lipids to form an amorphous spread film upon said surface, while not adversely increasing surface tension. Effective reduction of surface tension is evidenced, as discussed below, in increased eustachian tube patency.

It has been found that the above-described clinically significant decrease in eustachian tube opening pressure and effective distribution of lipids can be effected by a mixture comprised of from about 99.99 to about 30 weight percent lipid surfactant and from about 70 to about 0.01 spreading agent. However, it is preferred, and increased effectiveness is provided by a mixture comprised of from about 99.99 to about 50 weight percent lipid surfactant and from about 50 to about 0.01 weight percent spreading agent, both based on total weight of the mixture. However, it is still further preferred that in practicing the method of the second embodiment of the present invention, the lipid surfactants are present in an amount of about 80 to 99.5 percent by weight and the spreading agents are present in an amount of about 0.5 to about 20 percent by weight, both based upon the total weight of said mixture. The mixture resulting from the combination of lipid surfactant(s), spreading agent(s) and therapeutically active agent and propellant forms lipid crystals which act as carriers for said therapeutically active agent. A metered dose of the mixture of lipid crystals is then administered, preferably via an external nasal airway, into a mammal upon which the method is practiced. A suitable bottle equipped with a metered dose valve and nasal administration adaptor is advantageously utilized for this purpose. However, all embodiments of the present invention also contemplate administration via oral inhalation of said mixture.

Upon administration of the lipid crystal mixture, the propellants, carry the lipid crystals in combination with therapeutically active agent(s) effective in the treatment of otitis media to the nasopharyngeal terminus of the eustachian tube whereupon the propellant(s) evaporate. The lipid crystals and therapeutically active agent is then deposited upon the tissues of the eustachian tube, including the epithelial lined lumen, whereupon the mixture forms an amorphous spread film effectively carrying said therapeutically active agent effective in the treatment of otitis media to the epithelial lining of the eustachian tube lumen and target tissues of the eustachian tube and middle ear. As stated in further detail below, the therapeutically active agent is advantageously selected to be effective in the treatment of otitis media. Therefore, the second preferred method of the present invention provides a method of administering therapeutically active agents directly to lumen surfaces of mammalian eustachian tubes, and also, by means of said eustachian tube lumen, to middle ear target tissues wherein said therapeutically active agents provide effective treatment for otitis media while, in addition, providing the same increased eustachian tube patency and performance as the first embodiment.

The lipid crystals deposited upon the lumen surfaces and air/liquid interface thereof are comprised of one or more lipids which are advantageously selected to demonstrate powerful surfactant activity and to serve as a carrier for selected therapeutic agent(s). In addition, the spreading agent deposited therewith provides effective distribution of the surfactant and therapeutic agent(s) throughout the lumen air/liquid surface to form an amorphous spread film thereupon resulting in substantial decreases in lumen opening pressure. In turn, the decrease in lumen opening pressure provides greater patency of the eustachian tube. Thus a resultant increase in fluid conduction/equalizing function of this anatomical structure is provided while simultaneously providing direct application of therapeutically active agent to target tissues of the auditory tube and middle ear.

The lipids utilized in practicing the method and process of the present invention may be advantageously selected to be phospholipids, neutral lipids or mixtures thereof. The phospholipids utilized may be further advantageously selected to be any phospholipid of the class known as phosphatidlycholine including any fully saturated diacyl phosphatidlycholine including 1,2 dipalmitoyl phosphatidylcholine (DPPC); a diacylphosphatidylglycerol; a diacylphosphatidylethanolamine; a diacylphosphatidylserine; a diacylphosphatidylinositol; sphingomyelin, Cardiolipin, lysophospholipid; a plasmalogen; a diether phosphonolipid; or a dialklyphospholipid.

The lipids utilized in practicing the method and process of the present invention may also be advantageously selected to be either plant or animal sterols. For example, cholesterol, cholecalciferol and ergosterol may be selected. In addition fatty acids, such as, for example, palmitic acid and oleic acid may also be selected.

The cholesteryl esters utilized in practicing the method of the present invention may be advantageously selected to be, for example, cholesteryl palmitate, cholesteryl oleate, cholesteryl stearate or mixtures thereof. Carbohydrates utilized in the present invention may be advantageously selected to be, for example, glucose, fructose, galactose, pneumogalactan, dextrose or mixtures thereof. Proteins especially suited and advantageously selected for use in the present invention include albumin, pulmonary surfactant specific proteins A or B or C or D, their synthetic analogs, and mixtures thereof.

As stated in further detail below, the therapeutically active agent is advantageously selected to be effective in the treatment of otitis media as well as agents effective in the treatment of the underlying causes thereof provoking said immune responses leading to the above-described inflammatory responses. For example, such agents may be selected to be effective in the treatment of mycotic, viral or bacterial infections, (as well as combinations thereof) underlying and causative of said inflammatory reactions. Therefore, the second preferred method of the present invention provides a method of administering therapeutically active agents directly to the epithelial lining of the eustachian tube wherein said therapeutically active agents provide effective treatment for the subject inflammatory condition such as, for example edema—as well as the underlying causes thereof— while, simultaneously, the mixture of lipid crystals act to directly and effectively decrease the surface tension of the lumen.

In a first alternate embodiment of the present invention, a compound, process and method is disclosed providing administration of therapeutically active agents, effective in the treatment of otitis media, directly to mammalian eustachian tube and middle ear target tissues as well as a process for preparing a medicament for providing such treatment. In practicing the method and process of the first alternate embodiment of the present invention, a mixture of one or more lipid surfactants, one or more therapeutically active agent(s), effective in the treatment of otitis media, and/or the underlying cause thereof, and one or more propellants—in which said lipid surfactant and therapeutically active agents are not soluble—is prepared. The lipid surfactant is selected from the group consisting of sterols, lipids, fatty acids, cholesteryl esters, phospholipids, carbohydrates and proteins. The therapeutic agent may be selected from any of the afore or below-mentioned therapeutically active agents so as to provide desired therapeutic effects (regarding treatment of inflammatory conditions and the causative agents thereof). In such embodiments the mixture of lipids is comprised of a lipid surfactant and a therapeutic agent and the lipid surfactant and therapeutic agent are advantageously selected to be present in the same weight ratios as those described above and below in regards to those embodiments incorporating surfactant/spreading agent components—the therapeutic agent being present in the same respective weight percentage range as the spreading agent in such embodiments. For example, an effective result may be provided by a mixture comprised of from about 99.99 to about 30 weight percent lipid surfactant and from about 70 to about 0.01 therapeutic agent. Increased effectiveness is provided by a preferred mixture comprised of from about 99.99 to about 50 weight percent lipid surfactant and from about 50 to about 0.01 weight percent therapeutically active, both based on total weight of the mixture. However, it is still further preferred said mixture may be comprised of from about 80 to about 99.5 weight percent lipid surfactant and from about 20 to about 0.5 weight percent therapeutically active agent, based upon total weight of said mixture.

In practicing the first alternative embodiment, the therapeutically active agent may be selected as a pharmacologic agent which, in addition, is also selected from the group consisting of sterols, lipids, fatty acids, cholesteryl esters, phospholipids, carbohydrates and proteins. In such embodiments, the therapeutically active agent acts in accordance with its own pharmacologic function, as well as providing spreading agent function.

As described above, the therapeutic agent is selected to be present within the above-described weight ranges and in an amount sufficient to treat the afore-mentioned otitis media inflammatory condition and/or causative agents. The remainder of the mixture is comprised of one or more of the above-described lipid surfactants which act to reduce the surface tension of the liquid/air interface of the epithelial lining of the eustachian tube, while the therapeutically active agent provides treatment of the inflammatory condition effecting the eustachian tube, and/or the causative agents thereof. Upon evaporation of the propellant, an aerosolized mixture of lipid crystals is formed.

Upon administration of the mixture of lipid crystals and therapeutic agent to the eustachian tube via, for example, a metered dose bottle, the lipid crystal come into contact, and form an amorphous spread film upon the air/liquid interface resident upon the epithelial lining thereof. The surfactant spread film reduces the surface tension of the lumen while simultaneously delivering the therapeutic active agents to the afore-mentioned target tissues. The propellants may be advantageously selected to be fluorocarbon propellants such as, for example, chlorofluorocarbon propellants, hydrofluorocarbons or mixtures thereof. The present invention contemplates the use of carbon dioxide as a propellant as a suitable propellant. It is also contemplated that the present invention may incorporate and select any pharmaceutical grade, hypo-allergenic propellant in which the other components of the mixture are not soluble—the propellant, lipids, spreading agents and therapeutically active agents must be selected so none of the afore-mentioned surfactants, spreading agents or therapeutically active agents are soluble, and thus dissolved, within the propellant. The propellant is thus selected in order to enable the formation of the aerosolized mixture of lipid crystals, discussed below.

DETAILED DESCRIPTION OF THE INVENTION

Throughout this specification and claims, the phrase "therapeutically active agent" includes any substance which is capable of altering a biologic, physiologic and/or immunologic function, in nature or degree and includes those substances generally referred to pharmacologic agents, drugs and gene therapy agents; the term "fluorocarbons" includes the class of both chlorofluorocarbons and hydrofluorocarbons; the term lipids includes the class of phospholipids including, but not limited to PC, PG, PE, PI and Cardiolipin; and the phrase "spreading agent(s)" refer to and includes PG, PE, PS, PI, Sph., Card., lysophospholipids, plasmalogens, dialkylphospholipids, and all others in the class phospholipid as well as cholesteryl esters (like CP), proteins and carbohydrates.

Throughout this specification and claims, the phrase "spreading agent(s)" refers to compounds, as listed above, which assist the one or more lipid surfactants such as, for example, DPPC, in rapidly adsorbing and forming an amorphous spread film on air/liquid interfaces such as that found upon the epithelial lined lumen of the auditory tube. In addition, the compounds referred to as "spreading agent(s)", together with the one or more lipids, are responsible for achieving and maintaining biophysical properties including, but not limited to, reduction of intermolecular attractive forces, surface tension, and the resultant attractive forces generated thereby, that tend to cause opposed surfaces, such as the lateral and medial epithelial lined lumen walls of the auditory tube, to adhere to each other. As discussed below, in certain preferred embodiments of the present invention, the therapeutically active agent(s) is advantageously selected from the group consisting of sterols, lipids, fatty acids, cholesteryl esters, phospholipids, carbohydrates, and proteins, all in powder form. In such embodiments, the therapeutic agent(s) provides, in addition to the above-described pharmacologic effects, the functions of the spreading agent (without need for a separate spreading agent.)

The major lipid component utilized in practicing a preferred embodiment of the present invention is advantageously selected to be phospholipid 1,2 dipalmitoyl, phosphatidlycholine (DPPC). DPPC is the most surface active of the phospholipids or any of the subclass of fully saturated acyl chain phospholipids. That is to say that DPPC, in combination with any spreading agent(s) disclosed herein, has a maximum effect in reducing surface tension at an air/liquid interface.

Another, minor lipid component that also acts as a spreading agent for the major component is advantageously selected to be diacylphosphatidylglycerol (PG). The number of carbon atoms in the acyl chains R and R', (see PG formula below) can vary between 8 and 22 and may or may not be fully saturated. DPPC and PG can be synthesized. However, since DPPC and PG are the main phospholipid constituents of cells, they are also readily extractable from such cells by non-polar solvents, i.e., chloroform, ether, acetone. DPPC's structural formula is:

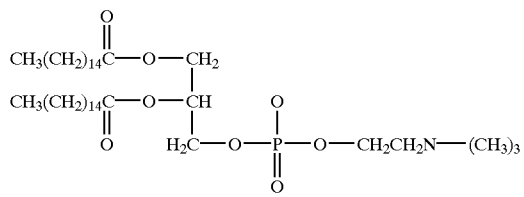

and PG's structural formula is:

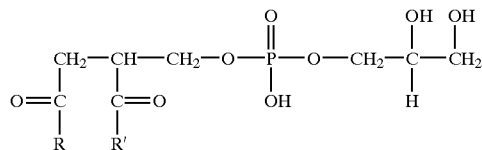

Phospholipids such as DPPC and CP may be obtained commercially, in a highly purified form from Fluka Chemical Co. of Ronkonkoma, N.Y.; Sigma Chemical CO. of St. Louis Mo.; and Avanti Polar Lipids of Birmingham, Ala. and Primedica of Cambridge, Mass.

DPPC and PG are preferred component(s) advantageously utilized in the present inventions methods for administering therapeutically active agents to the middle ear and auditory tube. In addition, these lipids increase the pressure equalizing performance of the auditory tube by direct result of their surfactant qualities. DPPC may be selected to be present in the composition over a fairly wide range. It is preferred that weight percentages of from about 80% to about 99.5% DPPC by is selected. However, the DPPC component may be selected to be present in an amount of from about 99.99% to about 50% by weight without undue interference in desired properties needed for drug delivery and surfactant activity.

Throughout this specification and in the claims, the phrase "increasing pressure equalization performance of the auditory tube" and "increasing the pressure equalization performance of the eustachian tube" both refer to the increased ease and ability of a mammal upon which the present method is practiced, to utilize the pathway provided by the lumen of the eustachian tube to equalize the pressure of the middle ear with ambient pressure surrounding the mammal. The increased ease and ability is the result of the decrease in opening pressure of the lumen of the mammalian eustachian tube provided by the present invention.

Another lipid that can be utilized in practicing the methods of the present invention is cholesteryl palmitate (CP), which also serves as a spreading agent. This cholesteryl ester is a neutral lipid which belongs to a class of organic compounds that are also cell constituents and are extractable by non-polar solvents such as chloroform, methanol, ether, etc. The structural formula of CP is:

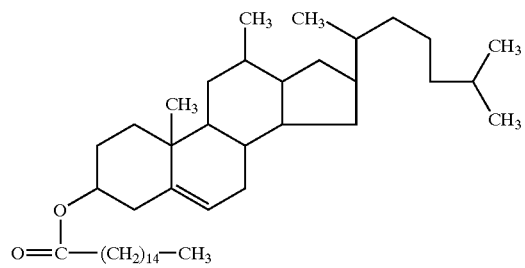

CP may be obtained commercially in a highly purified form from Fluka Chemical Co. and Sigma Chemical Co. The CP component constitutes a minor portion of the composition. It is selected to be present in a weight percentage sufficient so as to enable effective spread and distribution of the lipid upon the mucosal surfaces. It is preferred that the CP component be selected to be present in an amount ranging from about 0.5% to 20% by weight. Also, the preferred ratio of DPPC to CP is from about 99.5 DPPC to 0.5 CP by weight. However, the CP component may be selected to be present in an amount of from about 50 to about 0.01% by weight and the DPPC component may be selected to be percent in an amount of from about 99.99% to about 0.50 weight % without undue interference in desired properties needed for drug delivery and surfactant activity.

The term "therapeutically active agent" and "therapeutically active agent effective in the treatment of otitis media," as utilized in and throughout this specification and claims, refers to those drugs effective in treatment of otitis media including, but not limited to anti-inflammatory agents including, for example, betamethasone, including, for example, betamethasone dipropionate and betamethasone valerate as well as all other effective formulations; de-congestive agents such as phenylephrine, including, for example, phenylephrine HCL and phenylephrine bitartrate and all other effective formulations thereof; antibiotics including, for example erythromycin, amoxicillin, zythromax, and augmentin (amoxicillin and clavuliic acid) in all of their effective formulations and gene therapy agents. Such gene therapy agents, as the term is used herein, refers to a biochemical substance—as well as vectors thereof—selected from the group including, but not limited to, proteins, peptides or amino acids; nucleic acids such as DNA, including full length genes or fragments thereof derived from genomic, cDNA, or artificial coding sequences, gene regulatory elements, RNA including mRNA, tRNA, ribosomal RNA, ribozymes and anitsense RNA, oligonucleotides, oligoribonucleotides, deoxyribonucleotides and ribonucleotides as such agents may exist as isolated and purified compounds or in unpurified mixtures, such as tissue, cell or cell lysate. In addition, such agents may be naturally occurring, synthetic, or a mixture thereof. The term "all of their effective formulations" as used throughout this specification and in the claims refers to those specific species of a particular therapeutic agent effective in the treatment of otitis media.

The combination of lipid component(s) and spreading agent component(s) disclosed herein, may be referred to, collectively, as the "carrier" when said combination is mixed with a therapeutically active agent so as to act as a carrier therefore. When practicing the method of the present invention wherein therapeutically active agents are administered directly to mammalian eustachian tube and middle ear tissues, it is preferred that carrier, the mixture of one or more lipids and one or more spreading agents, be comprised of a mixture of DPPC and CP in a 200:1 ratio (by weight). However, it has been found that a ratio range of from 5:1 to 300:1 (DPPC/CP) will also produce an effective carrier for this embodiment. If, for example, the therapeutic agent is selected to be betamethasone, the weight ratio of betamethasone to carrier (DPPC/CP) is advantageously selected to be 1 microgram betamethasone to 5 milligrams carrier. However, it has been found that a weight ratio range of 0.5 to 1000 micrograms betamethasone/5 milligrams carrier yields an effective and functional mixture.

In certain embodiments of the present invention, the therapeutically active agent is advantageously selected from the group consisting of sterols, lipids, fatty acids, cholesteryl esters, phospholipids, carbohydrates, and proteins, all in powder form. In such embodiments, in addition to acting as pharmacologic agents, drugs or a gene therapy modality, the therapeutically active agent also serves as a spreading agent. In such instances, any of the afore-mentioned surfactants of the present invention may be combined with a therapeutic agents selected from the above-identified group at the same weight ratio ranges selected for spreading agent/surfactant mixtures. Upon administration (and evaporation of propellant) a mixture of lipid crystals is formed that acts to decrease opening pressure of the eustachian tube while simultaneously carrying the therapeutically active agent to target tissues of the eustachian tube and middle ear.

When practicing the method of the present invention wherein the therapeutically active agent is selected to be phenylephrine it is preferred to select the weight ratio of phenylephrine to carrier to be 160 micrograms/995 milligrams. However, it has also been found that a weight ratio range of from 50 to 5000 micrograms (phenylephrine): 995 to 900 milligrams carrier, respectively, forms an effective mixture and functional mixture. The term "effective and functional mixture" as utilized throughout this application and in the claims refers to the effectiveness of the mixture of lipid crystals in combination with said therapeutically active agent resulting from the combinations disclosed herein in: (a) reaching the target tissue of the eustachian tube and middle ear; (b) reducing the surface tension thereupon; and (c) delivering a uniform dose of therapeutic agent directly to and effectively spreading upon said tissues so as to effectively bring symptomatic relief and/or resolution of the afore-mentioned pathological conditions including otitis media.

When practicing the method of the present invention wherein the therapeutically active agent is selected to be the antibiotic erythromycin, the ratio of erythromycin to carrier is advantageously selected to be 200 mg antibiotic to 800 mg carrier (DPPC/CP) by weight. However, a weight range of from 50 to 200 mg erythromycin: from 950 to 800 mg carrier, respectively, has been found to be fully effective in practicing the present method.

The fluorocarbon propellants utilized in practicing certain preferred embodiments of the method of the present invention, namely: trichlorodifluoromethane, dichlorodifluoromethane, and tetrafluoromethane or mixtures thereof, which are commercially available from Union Carbide Corp., Danbury, Conn. and Armstrong Laboratories, West Roxbury Mass. are advantageously selected for formation of the lipid crystalline figures of the present invention. The fluorocarbon propellants are present over a range of 2 to 30 times the amount, by weight, of lipid, but components of lipid and fluorocarbon propellants both are needed in order to obtain the required lipid crystalline figures.

In practicing the methods of the present invention wherein therapeutically effective agents are administered directly to the middle ear for the treatment of otitis media, DPPC is advantageously selected as the major lipid component since the amphoteric nature of this phospholipid allows the molecule to act as a carrier for any drug or therapeutic agent. However, the presence of a charge on other lipid components (a negative charge on PG, for example) would alter and further improve the carrying capacity of the lipid crystals for a particular therapeutic agent.

In addition to erythromycin and amoxicillin, the method of the present invention also contemplates selecting zythromax and Augmentin (amoxicillin+clavulinic acid) as antibiotic therapeutic agents. However, because of the highly amphoteric nature of the carrier utilized herein, the use of any presently known and available, as well as antibiotic developed in the future capable of providing effective treatment of infections of the middle ear and eustachian tube are contemplated and fully functional with the methods and compositions herein.

EXAMPLE 1

The aerosolized drug delivery system of the present invention was prepared from chromatographically pure (greater than 99%) DPPC and CP. Both materials were purchased from suppliers on the commercial market where they are available from several chemical supply houses. Specifically, the DPPC and CP were purchased from Sigma Chem., St Louis, Mo. All purchased materials were checked for purity by standard chromatographic analysis. The betamethasone utilized in this example was also purchased from Sigma Chemical. The DPPC and CP were then mixed in the dry powder form in a weight ratio of 200:1 (DPPC:CP). To 5 milligrams of the resultant carrier, 1 microgram of betamethasone was added in order to yield a weight ratio of 5000:1 (carrier: betamethasone). Then 5 grams of this mixture was suspended in 55 grams of the first propellant, trichloromonofluoromethane (P11) and subdivided into 30 ml. Wheaton plastic-coated glass bottles with a 20 mm neck finish. Valois metered dose valves were then crimped onto each bottle through which 40 gms of the second propellant, dichlorodifluoromethane (P12), was passed. The filled bottles were then gently shaken to disperse the solids that are insoluble in the propellants. The bottles were thereafter immersed in a water bath to test for leaks and then fitted with a nasal administration adapter. The suspension was homogenous. After standing at room temperature for about three days, a pellicle forms on top of the propellants but is easily re-suspended by gentle shaking. The size of the metering valve can be varied to deliver from 1 mg up to 5.4 mg of the DPPC:CP:Betamethasone aerosolized mixture. However, metered dose valves having a greater dosing range are also contemplated and can be utilized in other embodiments of the present invention.

EXAMPLE II

The aerosolized drug delivery system of the present invention was prepared from chromatographically pure (greater than 99%) DPPC and CP. Both materials were purchased from suppliers on the commercial market where they are available from several chemical supply houses. Specifically, the DPPC and CP were purchased from Sigma Chem., St Louis, Mo. The phenylephrine utilized in this example can also be purchased from Sigma Chem., St Louis, Mo. All purchased materials were checked for purity by standard chromatographic analysis. The DPPC and CP were then mixed in the dry powder form in a weight ratio of 200:1 (DPPC:CP). Thereafter, to 995 milligrams of the resultant carrier, 160 micrograms of phenylephrine was added so as to yield an approximate 6200:1 weight ratio of carrier to phenylephrine. Then 5 grams of the resultant mixture (DPPC/CP/phenylephrine) was suspended in 55 grams of the first propellant, trichloromonofluoromethane (P11) and subdivided into 30 ml. Wheaton plastic-coated glass bottles with a 20 mm neck finish. Valois metered dose valves were then crimped onto each bottle through which 40 gms of the second propellant, dichlorodifluoromethane (P12), was passed. The filled bottles were then gently shaken to disperse the solids that are insoluble in the propellants and nasal administration adaptors. The bottles were immersed in a water bath to test for leaks and then fitted with a nasal administration adapter. The suspension was homogenous. After standing at room temperature for about three days, a pellicle forms on top of the propellants but is easily re-suspended by gentle shaking. The size of the metering valve can be varied to deliver from 1 mg up to 5.4 mg of the DPPC:CP: phenylephrine aerosolized mixture. However, metered dose valves having a greater dosing range are also contemplated and can be advantageously utilized in practicing the methods of the present invention.

EXAMPLE III

The aerosolized drug delivery system of the present invention was prepared from chromatographically pure (greater than 99%) DPPC and CP. Both materials were purchased from suppliers on the commercial market where they are available from several chemical supply houses. Specifically, the DPPC and CP were purchased from Sigma Chem., St Louis, Mo. The erythromycin utilized in this example can also be purchased from Sigma Chem., St Louis, Mo. All purchased materials were checked for purity by standard chromatographic analysis. The DPPC and CP were then mixed in the dry powder form in a weight ratio of 200:1 (DPPC:CP). Thereafter, to 800 milligrams of the resultant carrier, 200 milligrams of erythromycin was added so as to yield an approximate 4:1 weight ratio of carrier to erythromycin. Then 5 grams of the resultant mixture (DPPC/CP/erythromycin) was suspended in 55 grams of the first propellant, trichloromonofluoromethane (P11) and subdivided into 30 ml. Wheaton plastic-coated glass bottles with a 20 mm neck finish. Valois metered dose valves were then crimped onto each bottle through which 40 gms of the second propellant, dichlorodifluoromethane (P12), was passed. The filled bottles were then gently shaken to disperse the solids that are insoluble in the propellants. The bottles were immersed in a water bath to test for leaks and then fitted with a nasal administration adapter. The suspension was homogenous. After standing at room temperature for about three days, a pellicle forms on top of the propellants but is easily re-suspended by gentle shaking. The size of the metering valve can be varied to deliver from 1 mg up to 5.4 mg of the DPPC:CP: erythromycin aerosolized mixture. However, metered dose valves having a greater dosing range are are also contemplated and can be advantageously utilized in practicing the methods of the present invention.

EXAMPLE IV

The aerosolized drug delivery system of the present invention was prepared from chromatographically pure (greater than 99%) DPPC, PG and CP. All of these materials were purchased from suppliers on the commercial market where they are available from several chemical supply houses. Specifically, the DPPC, CP and PG were purchased from Sigma Chem., St Louis, Mo. The erythromycin utilized in this example can also be purchased from Sigma Chem. All purchased materials were checked for purity by standard chromatographic analysis. The DPPC, PG and CP were then mixed in the dry powder form in a weight ratio of 7:1:0.35 (DPPC:PG:CP). Thereafter, to 800 milligrams of the resultant carrier, 200 milligrams of erythromycin was added so as to yield an approximate 4:1 weight ratio of carrier to erythromycin. Then 5 grams of this mixture was suspended in 55 grams of the first propellant, trichloromonofluoromethane (P11) and subdivided into 30 ml. Wheaton plastic-coated glass bottles with a 20 mm neck finish. Valois metering valves were crimped onto each bottle through which 40 gms of the second propellant, dichlorodifluoromethane (P12), was passed. The filled bottles were then gently shaken to disperse the solids that are insoluble in the propellants. The bottles were thereafter immersed in a water bath to test for leaks and then fitted with a nasal administration adapter. The suspension was homogenous. After standing at room temperature for about three days, a pellicle forms on top of the propellants but was easily resuspended by gentle shaking. The size of the metering valve can be varied to deliver from 1 mg up to 5.4 mg of the DPPC:PG:CP: erythromycin aerosolized mixture.

EXAMPLE V

Chromatographically pure DPPC and CP (99% pure) were obtained from Avanti Polar Lipids Co. of Birmingham, Ala. and Sigma Chemical Co. of St. Louis, Mo.

DPPC and CP were mixed in a weight ratio of 200:1 (DPPC:CP). Then 5 grams of this mixture was suspended in 55 grams of the first propellant, trichloromonofluoromethane (P11) and subdivided into 30 ml. Wheaton plastic-coated glass bottles with a 20 mm neck finish. Valois metering valves were crimped onto each bottle through which 40 gms of the second propellant, dichlorodifluoromethane (P12), was passed. The filled bottles were then gently shaken to disperse the solids that are insoluble in the propellants. The bottles were thereafter immersed in a water bath to test for leaks and then fitted with a nasal inhalation adapter. The suspension was homogenous. After standing at room temperature for about three days, a pellicle forms on top of the propellants but was easily re-suspended by gentle shaking. The size of the metering valve can be varied to deliver from 5.4 mg up to 1.0 mg of the DPPC:CP aerosolized mixture.

The afore-described Examples "I" through "IV" are specific embodiments of the aerosolized drug delivery system utilized in practicing the method of the present invention. Each of the afore-mentioned Examples "I" through "IV" are administered by releasing a metered dose of the mixtures, by means of a nasal administration adaptor, through the nose. The aerosolized mixture, propelled by the above-described propellants, is then deposited about the anterior terminus of the eustachian tube at its communication with the nasopharynx. Thereafter, the crystalline lipid figures come in contact with mammalian auditory tube tissue and, forms an amorphous spread film layer upon the air/liquid interface resident upon the epithelial lined lumen. The spread film, in turn, spreads both the surfactant and the therapeutic agent carried thereby throughout the lumen of the tube and upon the air/liquid interface resident upon the epithelial lining of the tissues of both the auditory tube and middle ear.

In the above-described Example "I", wherein the therapeutically active agent is the anti-inflammatory betamethasone, the agent acts directly upon the auditory tube itself, reducing the excess mucoid secretions and swelling of the auditory tube characteristic of OME. Both excess mucoid secretions and inflammatory swelling of the tube substantially increase auditory tube opening pressure, or, in other words, both mucoid secretions and tissue swelling tend to increase the force required to open the lumen and form a patent duct between the middle ear and nasopharynx. However, DPPC and/or DPPC/PG lipids act independently of selected therapeutic agent(s) to reduce the surface tension of the lumen by reducing the intermolecular and surface charges found at the air/interface of the secretion covered lumen.

The present invention also contemplates the use of antibiotics such as, for example, erythromycin (Example "III" and "IV"), amoxicillin, zythromax and augmentin (amoxicillin+clavulinic acid). In such embodiments, the DPPC and/or DPPC/PG act to introduce such drugs to the auditory tube and middle ear in the same manner as described immediately above in regards to anti-inflammatory agents. However, while DPPC and DPPC/PG aerosolized mixtures act as carriers for such drugs, they also continue to provide the decrease in surface tension and opening pressure of the eustachian tube. Therefore, in instances in which the method of the present invention is utilized to treat a bacterial infection of the middle ear, direct application of antibiotic therapy to the tympanic cavity/eustachian tube bacterial source, and increased patency of the auditory tube is provided.

In Example "V", above, preparation of an aerosolized mixture of lipid crystals for use in practicing the method of the present invention is disclosed that is advantageously formulated for enhancing pressure equalization performance of mammalian eustachian tubes without the use of a therapeutically active agent. In practicing the second preferred embodiment of the present invention, the aerosolized mixture, propelled by the above-described propellants, is deposited about the anterior terminus of the eustachian tube at its communication with the nasopharynx. Thereafter, the crystalline lipid figures come in contact with auditory tube and form an amorphous spread film layer upon the air/liquid interface of the epithelial lined lumen which, in turn, spreads the lipid mixture throughout the lumen of the tube and into the middle ear. At the same time, surface tension of an air/liquid interface located upon the eustachian tube's epithelial lined lumen is reduced to provide said increased performance. In this example, a process, composition and method of enhancing pressure equalization performance of mammalian eustachian tubes is disclosed wherein surface tension of an air/liquid interface located upon the eustachian tube's epithelial lined lumen is reduced to provide said increased performance. However no therapeutically active agent is included in the aerosolized mixture or contemplated in this embodiment. Increased auditory tube patency is provided by means of interaction of the surfactant/spreading agent combination alone. However, in many instances, especially in the absence of infection and/or inflammatory disease, use of anti-inflammatory and antibiotics may not be necessary. As stated above, a principal cause of OME is thought to be reduced eustachian tube patency. Since OME, as opposed to acute otitis media, occurs in the absence of infection, use of antibiotics would be of little to no value in the treatment of such pathology. In addition, for those embodiments and applications of the present invention specifically directed at enhancing performance of the auditory tube for individuals who experience equilibration difficulties (solely in connection with flying or diving), elimination of unnecessary drugs would be highly desirable.

Effect of Aerosolized Lipid Crystals on Passive Opening Pressure of the Eustachian Tube in an Animal Model The aerosolized lipid crystal mixture described in "Example V", above, was administered, through the nose, to Mongolian Gerbils and Wistar Mice. Administration of the mixture resulted in a reduction, from an initial opening pressure of 36.82+/−2.03 mmHG to 29.16+/−2.67—an approximately 18% reduction in the Mongolian Gerbils—and from an initial opening pressure of 43.1+/−1.43 mmHG to 32.1+/−2.21—a reduction in opening pressure of approximately 23% in Wister Mice—. Therefore, the composition and method of the present invention effectively increased eustachian tube patency by means of an exogenous nasally administered surfactant.

Effect of Aeoosolized Lipid Crystals With and Without Therapeutically Active Agent Upon OME Otitis media with effusion (OME) was developed in 75 gerbils by intra tympanic injection of 100-ug/mL solution of lipopolysaccharide derived from *Klebsiella pneumoniae*. The animals were grouped and the following drugs were sprayed intra nasally, prepared in an aerosolized metered dose inhaler (MDI) viz 1) Placebo (normal saline); 2) Surfactant alone (DPPC:CP (200:1); 3) Surfactant with betamethasone (5 mg carrier to 10 micrograms betamethasone dipriprionate); 4) Surfactant with phenylephrine (995 mg carrier to 160 micrograms phenylephrine HCl). In-vivo Typanometry and Micro-otoscopy was done on the $3^{rd}$, $5^{th}$, $7^{th}$, $9^{th}$, $10^{th}$, $12^{th}$, $15^{th}$, $16^{th}$, $22^{nd}$ and $30^{th}$ days after the development of OME. Resolution of OME was observed by micro-otoscopy on the $6^{th}$, day in the surfactant with betamethasone group, on the $10^{th}$ day with the surfactant alone group, and on the $16^{th}$ day for all other groups. The experimental results demonstrate the effectiveness of those methods of the present infection utilizing anti-inflammatory agents, as well as those utilizing the disclosed aerosolized lipid crystals alone, in providing effective treatment of otitis media.

Structural Characteristics

Particle Size and Gross Configuration

Particle size of the nebulized crystals produced and utilized in practicing the present invention is, as discussed below, is important for effective administration. The size (diameter) of the lipid crystals were therefore determined utilizing a cascade impactor. Flow through the impactor was adjusted to be substantially identical to the flow from a nebulizer utilized in practicing the disclosed method. All of the lipid crystals were found to have a diameter equal to or less than 16 microns. The diameter of about 95 percent of the particles were found to be equal to or less than 4 microns in diameter. Of the particles found to be 4 microns or less, half were, in fact, 1 micron in diameter. The mean diameter demonstrated by the lipid crystals utilized in the method of the present invention was 1.75+/−0.25 microns.

Micronization may be advantageously utilized in order to insure reduced particle size. Therefore, the methods of the present invention also contemplate the use of a micronization mill such as, for example, the "DYNO" mill, type KDL, manufactured by Glen Mills Inc., of New Jersey in the preparation of the aerosolized mixture. For example, approximately 13.33 grams of CP and 83 g of DPPC powder were weighed and transferred to a bead mill within the milling chamber of a DYNO mill (having about 480 cc of glass beads). The chamber was then sealed. Thereafter, 1 liter of HFC-134a was added and the system chilled to about −10° C. at a pressure of approximately 65 psi. Milling was achieved in about 1 hour. Thereafter, the resultant slurry was utilized to fill 15 mil epoxy phenolic lined aluminum cans (Safet Embamet, St. Florantine, France), fitted with Valois metering valves (DFI/ACT/kematal, Valois, Le Neuborg, France with Micron-4 acuators (also Valois). A laser particle sizer, model 2600c, Malvern Instruments, Inc., was thereafter utilized to size the resultant particles as shown in Table "1", below. This data indicates that approximately 90% of the particles emitted fro the valve and actuator system are under 7 µm or less in diameter. The mean diameter (arithmetic mean) is approximately 5 µm and the mass median aerodynamic diameter (MMAD) is about 3.4 µm with a geometric standard deviation (GSD) of about 0.5. Particle size results in physically unstable dispersions should change dramatically over a few days of undisturbed storage.

TABLE 1

Particle Size Summary

| Day Number | 90 Percentile | 50 Percentile | % ≦ 10 µm | MMAD | GSD |
|---|---|---|---|---|---|
| 1 | 6.9 µm | 5.1 µm | 100 | 3.4 | 0.5 |
| 2 | 6.8 µm | 4.8 µm | 99.9 | 3.5 | 0.5 |
| 3 | 7.3 µm | 5.4 µm | 100.0 | 3.5 | 0.5 |
| 4 | 6.5 µm | 4.6 µm | 99.9 | 3.2 | 0.5 |
| 5 | 6.8 µm | 4.7 µm | 100.0 | 3.4 | 0.5 |
| Mean | 6.9 ± 0.3 µm | 4.9 ± 0.3 µm | 100.0 | 3.4 ± 0.1 | 0.5 |

Structural characteristics of the mixture of lipid crystals utilized in practicing the present invention were further assessed by capturing the aerosolized particles on standard scanning electron microscopic grids fixed to glass slides at 22° C., (dry). The lipids deposited on glass both as dry particles and as coalesced droplets. The latter evaporated immediately leaving dry lipid. The dry lipids, were fixed in osmium vapor ($O_sO_4$), coated and viewed with a scanning electron microscope. Crystalline figures about 100 angstroms thick, were grouped in clumps on the dry surface. This is a unique configuration.

Crystalline Structure

The mixture of one or more lipids, one or more spreading and one or more propellants disclosed in the present invention is especially formulated and combined to form a unique crystalline structure with physical dimensions highly advantageous to all embodiments. For example, the crystalline structure results in, as discussed above, a mean particle size of 1.75 microns. The minute physical dimensions of the individual nebulized particles enables the propellant utilized in practicing the present invention to easily and effectively transfer the disclosed mixture to and throughout the desired target tissue. A larger physical configurations such as, for example, a liposome, would not enable such diminutive particle size within and such effective physical transport by the propellant.

Functional Properties

The aerosolized mixture of the present invention is crystalline. The crystalline nature of the mixture imparts increased efficiency of particle dispersion within the aerosol mist applied by means of a metered-dose nebulizer. Upon application, the propellant, such as, for example a fluorocarbon medium, (either chlorofluorocarbon or hydrofluorocarbon), vaporizes rapidly and the DPPC/CP, DPPC/CP drug, DPPC/PG drug or DPPC/PG/CP drug dispersion deposits on an aqueous surface at 37° C., initially in the crystalline form, and then, instantaneously, spreads over the surface as an amorphous surface film. In embodiments wherein a therapeutic is combined with the carrier, the drug likewise is spread, throughout the aqueous surface.

The surfactant/spreading agent functions and characteristics of the method, process and composition of the present invention were tested as follows. Aerosolized crystalline figures of the present invention were impacted upon a liquid surface (normal saline solution, NSS) at 37° C., 100% humidity in a surface balance resulted in a rapid spreading of a principally amorphous film that covered the entire surface (18.1 cm$^2$). Surface tension of the film was measured during expansion and compression at 37° C., 100% humidity. Film expansion to 110.4 cm$^2$ produced a surface tension of 72 dynes/cm and compression to 18.1 cm$^2$ lowered surface tension to less than 1 dyne/cm.

The terms and expressions which have been employed in the foregoing specification are used therein as terms of description and not limitation, and there is no intention, in the use of such terms and expressions, of excluding equivalents of the features shown and described or portions thereof, it being recognized that the scope of the invention is defined and limited only by the following claims.

I claim:

1. A method of increasing and enhancing mammalian eustachian tube lumen patency and pressure equalization performance comprising administering a dose of a mixture of lipid crystals, as an aerosol, through an external airway of a mammal, said mixture being comprised of at least one lipid surfactant in an amount effective in lowering surface tension of an air/liquid interface resident upon epithelial tissue lining said lumen, at least one spreading agent in an amount effective in distributing said surfactant within said lumen and at least one propellant in which said surfactants and spreading agents are not soluble, said surfactants and said spreading agents being selected from the group consisting of sterols, lipids, fatty acids, cholesteryl esters, phospholipids, carbohydrates, and proteins, all in powder form;

whereupon, when said mixture is so administered, said propellants are evaporated from said mixture as said lipid crystals come into contact with, and deposit upon the epithelial lining of the eustachian tube and form an amorphous spread film thereupon so as to reduce the opening pressure of said tube.

2. The method of claim 1 wherein said amount of lipid surfactant is selected to be present in an amount of from about 50 to about 99.99 weight percent and wherein said spreading agent is selected to be present in an amount of from about 0.01 to about 50 weight percent.

3. The method of claim 1 wherein said lipid surfactant is selected to be present in an amount of from about 80 to about 99.5 weight percent and wherein said spreading agent is selected to be present in an amount of from about 0.5 to about 20 weight percent.

4. The method of claim 1 wherein a metered dose inhalation device is filled with said mixture of lipid crystals and thereafter said device is utilized to administer a metered dose of said mixture through an external nasal orifice of said mammal.

5. The method of claim 1 wherein a metered dose inhalation device is filled with said mixture of lipid crystals and thereafter said device is utilized to administer a metered dose of said mixture via oral inhalation.

6. The method of claim 1 wherein the sterols are cholesterol, ergosterol, cholecalciferol and mixtures thereof.

7. The method of claim 1 wherein the fatty acids are palmitic acid, oleic acid and mixtures thereof.

8. The method of claim 1 wherein the lipids are phospholipids, neutral lipids and mixtures thereof.

9. The method of claim 8 wherein the phospholipids are any of a class known as phosphatidylcholines.

10. The method of claim 9 wherein the phosphatidylcholine is any fully saturated diacyl phosphatidylcholine.

11. The method of claim 10 wherein the fully saturated diacyl phosphatidylcholine is 1,2 dipalmitoyl phosphatidylcholine.

12. The method of claim 8 wherein the phospholipid is a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphospholipid, and a mixture thereof.

13. The method of claim 1 wherein the carbohydrates are glucose, fructose, galactose, pneumogalactan, dextrose and mixtures thereof.

14. The method of claim 1 wherein the protein is selected from albumin and pulmonary surfactant specific proteins A or B or C or D and mixtures thereof.

15. The method of claim 1 wherein the cholesteryl ester is cholesteryl palmitate, cholesteryl oleate, cholesteryl stearate and mixtures thereof.

16. The method of claim 1 wherein the propellants are fluorocarbons.

17. The method of claim 16 wherein the fluorocarbon is a chlorofluorocarbon, hydrofluorocarbon and mixtures thereof.

18. The method of claim 1 wherein the propellant is carbon dioxide.

19. The method of claim 1 wherein the propellant is any pharmaceutical grade hypo-allergenic propellant in which neither the surfactant or spreading agent are soluble.

20. The method of claim 1 wherein 95 percent of said crystals are a particle size no greater than 4 microns in diameter.

21. A method of administering therapeutic agents, effective in the treatment of otitis media, directly to mammalian eustachian tube and middle ear tissues while simultaneously increasing and enhancing eustachian tube lumen patency and pressure equalization performance comprising administering a dose of a mixture of lipid crystals in combination with said therapeutic agents, as an aerosol, through an external airway of a mammal, said mixture being comprised of at least one lipid surfactant in an amount effective in lowering surface tension of an air/liquid interface resident upon epithelial tissue lining said lumen, at least one spreading agent in an amount effective in distributing said surfactants upon said interface within said lumen, at least one therapeutically active agent effective in the treatment of otitis media and at least one propellants, said surfactants and said spreading agents being selected from the group consisting of sterols, lipids, fatty acids, cholesteryl esters, phospholipids, carbohydrates, and proteins, said surfactants, spreading agents and therapeutically active agents all being in powder form and insoluble in the propellants, whereupon, when said mixture is so administered, said propellants evaporate from said mixture as said lipid crystals come into contact with, and deposit upon the epithelial lining of the eustachian tube and form an amorphous spread film thereupon so as to reduce the opening pressure of said tube while distributing said therapeutically active agent within said lumen and to said middle ear tissues.

22. The method of claim 21 wherein said lipid surfactant is selected to be present in an amount of from about 50 to about 99.99 weight percent and wherein said spreading agent is selected to be present in an amount of from about 0.01 to about 50 weight percent.

23. The method of claim 21 wherein said lipid surfactant is selected to be present in an amount of from about 80 to about 99.5 weight percent and wherein said spreading agent is selected to be present in an amount of from about 0.5 to about 20 weight percent.

24. The method of claim 21 wherein a metered dose inhalation device is filled with said mixture of lipid crystals in combination with said therapeutically active agent and thereafter said device is utilized to administer a metered dose of said mixture through an external nasal orifice of said mammal.

25. The method of claim 21 wherein a metered dose inhalation device is filled with said mixture of lipid crystals in combination with said therapeutically active agent and thereafter said device is utilized to administer a metered dose of said mixture by means of oral inhalation.

26. The method of claim 21 wherein the sterols are cholesterol, ergosterol, cholecalciferol and mixtures thereof.

27. The method of claim 21 wherein the fatty acids are palmitic acid, oleic acid and mixtures thereof.

28. The method of claim 21 wherein the lipids are phospholipids, neutral lipids and mixtures thereof.

29. The method of claim 28 wherein the phospholipids are any of a class known as phosphatidylcholines.

30. The method of claim 29 wherein the phosphatidylcholine is any fully saturated diacyl phosphatidylcholine.

31. The method of claim 30 wherein the fully saturated diacyl phosphatidylcholine is 1,2 dipalmitoyl phosphatidylcholine.

32. The method of claim 28 wherein the phospholipid is a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphospholipid, and a mixture thereof.

33. The method of claim 21 wherein the carbohydrates are glucose, fructose, galactose, pneumogalactan, dextrose and mixtures thereof.

34. The method of claim 21 wherein the protein is selected from albumin and pulmonary surfactant specific proteins A or B or C or D and mixtures thereof.

35. The method of claim 21 wherein the cholesteryl ester is cholesteryl palmitate, cholesteryl oleate, cholesteryl stearate and mixture thereof.

36. The method of claim 21 wherein said therapeutically active agent is an anti-inflammatory, antibiotic, decongestant and gene therapy agent.

37. The method of claim 36 wherein said anti-inflammatory agent is betamethasone.

38. The method of claim 36 wherein said antibioitic is erythromycin, amoxicillin, zythromax and amoxicillia/elavalanste potassium.

39. The method of claim 36 wherein said decongestant is phenylephrine.

40. The method of claim 21 wherein the propellants are fluorocarbons.

41. The method of claim 40 wherein the fluorocarbon is a chlorofluorocarbon, hydrofluorocarbon and mixtures thereof.

42. The method of claim 21 wherein the propellant is carbon dioxide.

43. The method of claim 21 wherein the propellant is any pharmaceutical grade, hypo-allergenic propellant in which neither the surfactant, spreading agent or therapeutically active agent are soluble.

44. The method of claim 21 wherein 95 percent of said crystals and a particle size no greater than 4 microns in diameter.

45. A method of administering therapeutic agents, effective in the treatment of otitis media, directly to mammalian eustachian tube and middle ear tissues while simultaneously increasing and enhancing eustachian tube lumen patency and pressure equalization performance comprising administering a dose of a mixture of lipid crystals in combination with said therapeutic agents, as an aerosolized mixture of lipid crystals, through an external airway of a mammal, said mixture being comprised of at least one lipid surfactant in an amount effective in lowering surface tension of an air/liquid interface resident upon epithelial tissue lining said lumen, at least one therapeutically active agent effective in the treatment of otitis media and at least one propellant, said lipid surfactants being selected from the group consisting of sterols, lipids, fatty acids, cholesteryl esters, phospholipids, carbohydrates, and proteins, said surfactants and therapeutically active agents all being in powder form and insoluble in the propellants, whereupon, when said mixture of lipid crystals is so administered, said propellants evaporate from said mixture as said lipid crystals come into contact with, and deposit upon the epithelial lining of the eustachian tube so as to reduce the opening pressure of said tube while distributing said therapeutically active agent within said lumen and to said middle ear tissues.

46. The method of claim 45 wherein said lipid surfactant is selected to be present in an amount of from about 50 to about 99.99 weight percent and wherein said therapeutically active agent is selected to be present in an amount of from about 0.01 to about 50 weight percent.

47. The method of claim 45 wherein said lipid surfactant is selected to be present in an amount of from about 80 to about 99.5 weight percent and wherein said therapeutically active agent is selected to be present in an amount of from about 0.5 to about 20 weight percent.

48. The method of claim 45 wherein a metered dose inhalation device is filled with said mixture of lipid crystals in combination with said therapeutically active agent and thereafter said device is utilized to administer a metered dose of said mixture through an external nasal orifice of said mammal.

49. The method of claim 45 wherein a metered dose inhalation device is filled with said mixture of lipid crystals in combination with said therapeutically active agent and thereafter said device is utilized to administer a metered dose of said mixture by means of oral inhalation.

50. The method of claim 45 wherein the sterols are cholesterol, ergosterol, cholecalciferol and mixtures thereof.

51. The method of claim 45 wherein the fatty acids are palmitic acid, oleic acid and mixtures thereof.

52. The method of claim 45 wherein the lipids are phospholipids, neutral lipids and mixtures thereof.

53. The method of claim 52 wherein the phospholipids are any of a class known as phosphatidylcholines.

54. The method of claim 53 wherein the phosphatidylcholine is any fully saturated diacyl phosphatidylcholine.

55. The method of claim 54 wherein the fully saturated diacyl phosphatidylcholine is 1,2 dipalmitoyl phosphatidylcholine.

56. The method of claim 52 wherein the phospholipid is a diacylphosphatidylglycerol, diacylphosphatidylethanolamime, diacylphosphatidylserine, diacylphosphatidylinositol, sphingomelin, Cardiolipin, lysophospholipid, plasmalogen, diether phosphonolipid, dialkylphospholipid, and a mixture thereof.

57. The method of claim 45 wherein the carbohydrates are glucose, fructose, galactose, pneumogalactan, dextrose and mixtures thereof.

58. The method of claim 45 wherein the protein is selected from albumin and pulmonary surfactant specific proteins A or B or C or D and mixtures thereof.

59. The method of claim 45 wherein the cholesteryl ester is cholesteryl palmitate, cholesteryl oleate, cholesteryl stearate and mixture thereof.

60. The method of claim 45 wherein said therapeutically active agent is an anti-inflammatory, antibiotic, decongestant or gene therapy agent.

61. The method of claim 60 wherein said anti-inflammatory agent is betamethasone.

62. The method of claim 60 wherein said antibiotic is erythromycin, amoxicillin, zythromax and amoxicillia/elavalanste potassium.

63. The method of claim 60 wherein said decongestant is phenylephrine.

64. The method of claim 45 wherein the propellants are fluorocarbons.

65. The method of claim 64 wherein the fluorocarbon is a chlorofluorocarbon, hydrofluorocarbon and mixtures thereof.

66. The method of claim 45 wherein the propellant is carbon dioxide.

67. The method of claim 45 wherein the propellant is selected to be any pharmaceutical grade, hypo-allergenic propellant in which neither the at least one surfactant or therapeutically active agent are soluble.

68. The method of claim 45 wherein the therapeutic agent is selected from the group consisting of sterols, lipids, fatty acids, cholesteryl esters, phospholipids, carbohydrates, and proteins.

* * * * *